(12) United States Patent
Azam et al.

(10) Patent No.: US 10,144,748 B1
(45) Date of Patent: Dec. 4, 2018

(54) ANTI-INFLAMMATORY ZINC(II) COMPLEX

(71) Applicant: KING SAUD UNIVERSITY, Riyadh (SA)

(72) Inventors: Mohammad Azam, Riyadh (SA); Saud Ibrahim Al-Resayes, Riyadh (SA); Faiyaz Shakeel, Riyadh (SA); Agata Trzesowska-Kruszynska, Lodz (PL); Rafal Kruszynski, Lodz (PL)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/916,208

(22) Filed: Mar. 8, 2018

(51) Int. Cl.
*C07F 3/06* (2006.01)
*A61K 33/30* (2006.01)
*A61P 29/00* (2006.01)

(52) U.S. Cl.
CPC .............. *C07F 3/06* (2013.01); *A61P 29/00* (2018.01)

(58) Field of Classification Search
CPC ............ C07F 3/06; A61P 29/00; A61K 33/30
See application file for complete search history.

(56) References Cited

U.S. PATENT DOCUMENTS

| | | |
|---|---|---|
| 5,637,311 A | 6/1997 | Pallenberg |
| 6,930,099 B2 | 8/2005 | Petrus |

OTHER PUBLICATIONS

Warad et al. J. Mol. Struct. 2014, 1062, 167-173 (Year: 2014).*
Xu et al. Nature 2008, 452, 56-61 (Year: 2008).*
Kia, R., et al., [N, N'-Bis(4-chlorobenzylidene)-2,2-dimethylpropane-1,3-diamine-K2N,N']-iodidocopper(I), Acta Crystal. Struct. 65:197 (2009).
Warad, I., et al., Design and Structural Studies of Diimine/CdX2 (X=Cl, I) Complexes Based on 2,2dimethyl-1,3-diaminopropane Ligand, J. Mol. Struct. 1062 pp. 167-173 (2014).

* cited by examiner

Primary Examiner — Amanda L Aguirre
(74) Attorney, Agent, or Firm — Richard C. Litman

(57) ABSTRACT

The anti-inflammatory zinc(II) complex, viz., crystalline bis(chloro)-(N,N'-(2,2-dimethylpropane-1,3-diyl)bis(1-(2-chlorophenyl)-methanimine))-zinc zinc(II) complex, may be used as an anti-inflammatory. The compound has the formula:

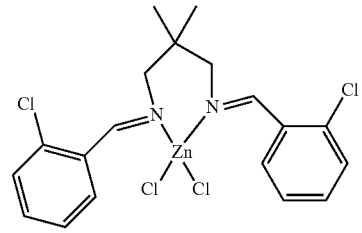

This complex is prepared by reaction of a Schiff base, namely, N,N'-bis(2-chlorobenzylidene)-2,2-dimethylpropane-1,3-diamine, with zinc chloride in alcohol to form a precipitate, which is removed by filtration, followed by slow evaporation of the filtrate to obtain the crystalline product. In vivo testing showed that the above zinc(II) complex exhibited good anti-inflammatory effect. It is thought that the present zinc-based anti-inflammatory avoids the gastrointestinal side effects of conventional NSAIDs due to the coordinated zinc complex.

1 Claim, 6 Drawing Sheets

ANTI-INFLAMMATORY ZINC(II) COMPLEX

BACKGROUND

1. Field

The disclosure of the present patent application relates to zinc-based coordination compounds, and particularly to an anti-inflammatory zinc(II) complex, namely, crystalline bis(chloro)-(N,N'-(2,2-dimethylpropane-1,3-diyl)bis(1-(2-chlorophenyl)methanimine))-zinc(II) complex.

2. Description of the Related Art

Zinc is the second most abundant trace element in the human body. Zinc is extremely important in the proper functioning of various enzymes involved in the regulation of cell metabolism, regulating cellular processes and cellular signaling pathways. The non-toxic and flexible coordination nature of zinc makes it highly adaptable for proteins and enzymes that carry out diverse biological functions. Zinc-containing complexes have demonstrated anticonvulsant, anti-diabetic, anti-inflammatory, and anticancer activities.

Non-steroidal anti-inflammatory drugs (NSAIDs) are among the most frequently used analgesic, anti-inflammatory and antipyretic agents. Unfortunately, these drugs are associated with detrimental side effects, particularly in the gastrointestinal tract and the kidney, thus making their use limited. Thus, an anti-inflammatory zinc(II) complex solving the aforementioned problems is desired.

SUMMARY

The anti-inflammatory zinc(II) complex, namely, crystalline bis(chloro)-(N,N'-(2,2-dimethylpropane-1,3-diyl)bis(1-(2-chlorophenyl)-methanimine))-zinc(II) complex, may be used as an anti-inflammatory. The compound has the formula:

This complex is prepared by reaction of a Schiff base, namely, N,N'-bis(2-chlorobenzylidene)-2,2-dimethylpropane-1,3-diamine, with zinc chloride in alcohol to form a precipitate, which is removed by filtration, followed by slow evaporation of the filtrate to obtain the crystalline product. In vivo testing showed that the above zinc(II) complex exhibited good anti-inflammatory effect. It is thought that the present zinc-based anti-inflammatory avoids the gastrointestinal side effects of conventional NSAIDs due to the coordinated zinc complex.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
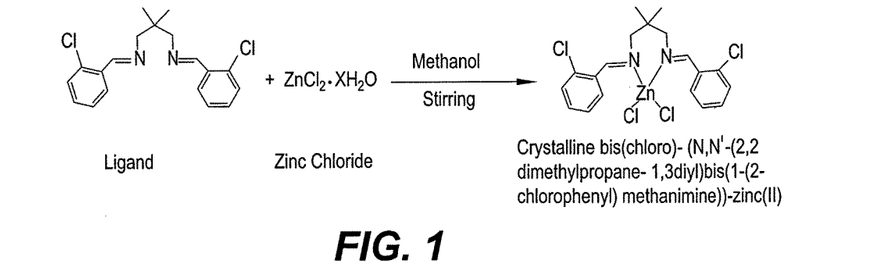
FIG. 1 is a reaction scheme showing the synthesis of the anti-inflammatory zinc(II) complex.
Figure 2:
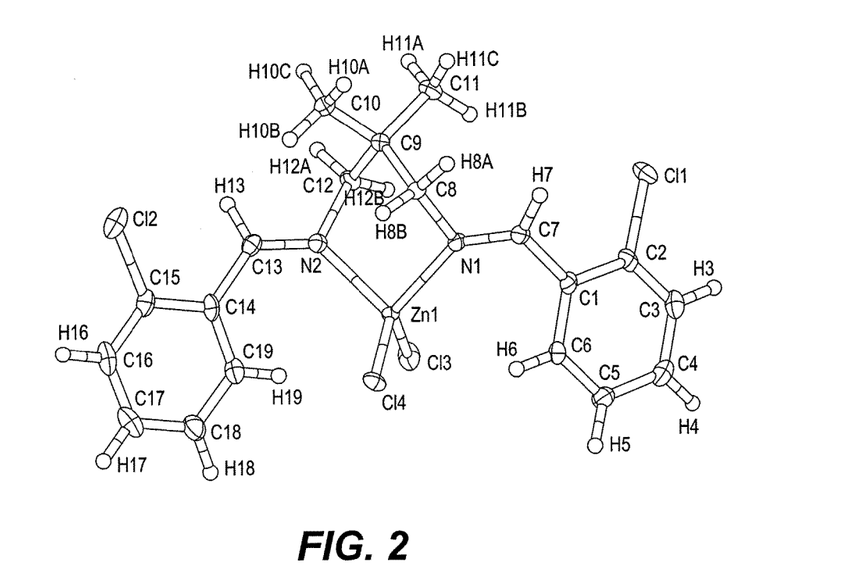
FIG. 2 is a 3D plot of the crystal structure of the anti-inflammatory zinc(II) complex synthesized as shown in FIG. 1, plotted with 50% probability of displacement ellipsoids and wherein hydrogen atoms are drawn as spheres of arbitrary radii.
Figure 3:
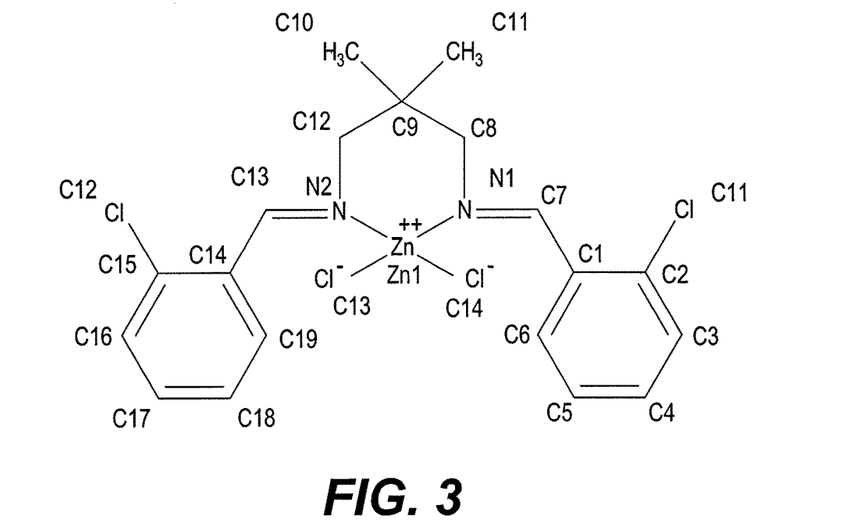
FIG. 3 is a numbering diagram showing numbering of the carbon, chlorine, and zinc atoms of anti-inflammatory zinc (II) complex.
Figure 4:
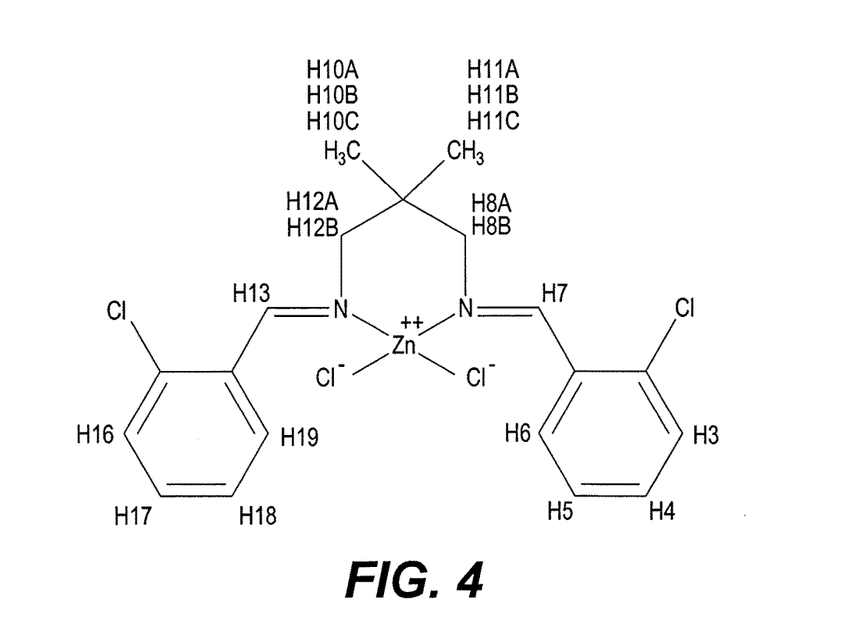
FIG. 4 is a numbering diagram showing numbering of the hydrogen atoms of anti-inflammatory zinc(II) complex.

The anti-inflammatory zinc(II) complex, viz., crystalline bis(chloro)-(N,N'-(2,2-dimethylpropane-1,3-diyl)bis(1-(2-chlorophenyl)methanimine))-zinc(II) complex, referred to herein as the zinc(II) complex (or "the zinc complex"), is prepared according to the reaction scheme set forth in FIG. 1. A pseudo-3-dimensional molecular structure is depicted in FIG. 2, with all atoms numbered. FIGS. 3 and 4 present two diagrams, where the formula in FIG. 3 includes numbering of the carbon, chlorine, and zinc atoms, while the formula in FIG. 4 includes numbering of the hydrogen atoms.

A crystal of the bis(chloro)-(N,N'-(2,2-dimethylpropane-1,3-diyl)bis(1-(2-chloro-phenyl)methanimine))-zinc(II) complex, with approximate dimensions of 0.075×0.069×0.066 mm, was mounted on a MiTeGen MicroMount mounting tool. Diffraction data was collected on a Bruker APEX II CCD diffractometer with w axis oscillation method using a wavelength of 1.54178 Å. The collected data were processed using ShelXTL crystallographic software for structural analysis, resulting in FIG. 2. The SHELXS, SHELXL and SHELXTL crystallographic software programs were used for all calculations. Atomic scattering factors were taken from the International Tables for Crystallography.

Example 1

Synthesis of Crystalline bis(chloro)-(N,N'-(2,2-dimethylpropane-1,3-diyl) bis(1-(2-chloro-phenyl)-methanimine))-zinc(II) Complex A solution of $ZnCl_2$ (90 mg, 0.66 mmol) in 10 ml methanol was added dropwise into the solution of the following Schiff base ligand:

(N,N'-bis(2-chlorobenzylidene)-2,2-dimethylpropane-1,3-diamine) (229 mg, 10 ml ethanol) under stirring for three hours. See FIG. 1. A white precipitate forms, and is removed by filtration. After storing the filtrate for few days, prismatic crystals are obtained after slow evaporation of the reaction mixture at room temperature. The crystalline complex is prismatic in form, and colorless.

Example 2

Analysis of the Crystalline Zinc(II) Complex

A plot of the crystalline zinc(II) complex structure is shown in FIG. 2, which depicts the crystal structure of the complex plotted with 50% probability of displacement ellipsoids from diffraction measurements. Hydrogen atoms are drawn as spheres of arbitrary radii. General crystal and structural data are set forth in Table 1, below.

As reflected in Table 1, crystalline bis(chloro)-(N,N'-(2,2-dimethylpropane-1,3-diyl)bis(1-(2 chlorophenyl) methanimine))-zinc has a monoclinic crystal system and a P2$_1$/c space group. The complex also is characterized by crystal lattice parameters of: a=10.0761(3) Å; b=15.4015(5) Å; c=13.8575(4) Å; β=103.1180(10°); V=2094.39(11) Å$^3$; and a Z value=4.

TABLE 1

Crystal and structure refinement data of Zn(II) complex

| Compound | 1 |
| --- | --- |
| Empirical formula | C$_{19}$H$_{20}$Cl$_4$N$_2$Zn |
| Formula weight | 483.54 |
| Crystal system, space group | monoclinic, P2$_1$/c (No. 14) |
| Unit cell dimensions [Å, °] | a = 10.0761(3) |
| | b = 15.4015(5) |
| | c = 13.8575(4) |
| | β = 103.1180(10) |
| Volume [Å$^3$] | 2094.39(11) |
| Z, Calculated density [Mg/m$^3$] | 4, 1.534 |
| F(000) | 984 |
| Crystal size [mm] | 0.075, 0.069, 0.066 |
| θ range for data collection [°] | 4.356 to 72.572 |
| Index ranges | −12 ≤ h ≤ 12, −18 ≤ k ≤ 19, −17 ≤ l ≤ 17 |
| Reflections collected/unique | 23219/4142 [R$_{(int)}$ = 0.0241] |
| Completeness [%] | 99.9 (to θ = 67°) |
| Data/restraints/parameters | 4142/0/237 |
| Goodness-of-fit on F$^2$ | 1.136 |
| Final R indices [I > 2σ(I)] | R1 = 0.0229, wR2 = 0.0559 |
| R indices (all data) | R1 = 0.0230, wR2 = 0.0559 |
| Largest diff. peak and hole [e · Å$^{−3}$] | 0.396, −0.297 |

Figure 5:
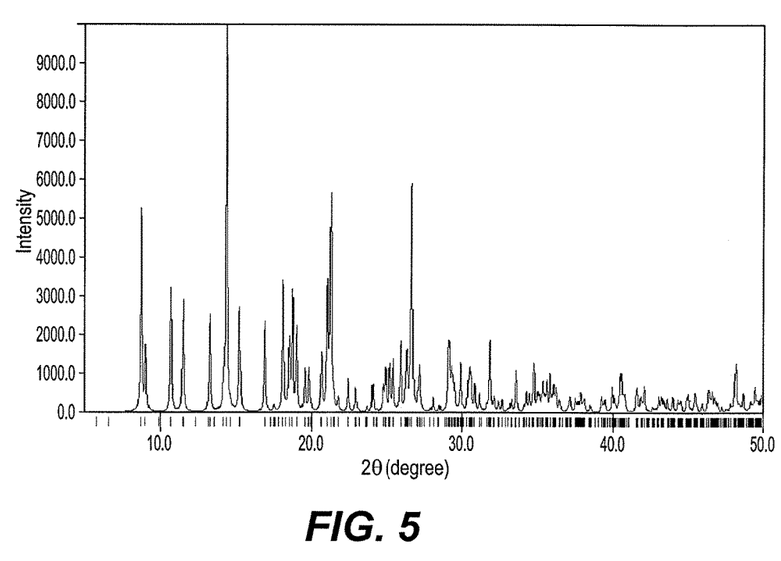
FIG. 5 is a plot of the X-ray diffraction pattern for anti-inflammatory zinc(II) complex.

The X-ray diffraction pattern of the complex is provided in FIG. 5. The compound is composed of the difunctional chelating bis(chloro)-(N,N'-(2,2-dimethylpropane-1,3-diyl) bis(1-(2-chlorophenyl)methanimine)) ligand, the Zn$^{2+}$ cation and two chloride anions. The molecule exhibits a pseudosymmetrical rotational axis going through the Zn1 and C9 atoms. The coordination environment of the atoms adopts slightly distorted tetrahedral geometry. The sum of interbond angles about the metal atom is 653.5°—close to the sum of these angles for an ideal tetrahedron (657°), and different from ideal values for square planar geometry (720°) or t-shape geometry (630°).

The 1-(2-chlorophenyl)methanimine moieties are distinctly distorted from planarity. The N=C—C$_{Ph}$—C$_{Ph}$ torsion angles are −32.9(2) and −35.4(2°). The analysis of C—N bond lengths shows that the double bonds are fully localized within the benzylideneamino moieties (Table 2).

TABLE 2

Selected structural data of Zn(II) complex [Å, °].

| Zn1—N2 | 2.0611(12) |
| --- | --- |
| Zn1—N1 | 2.0682(12) |
| Zn1—Cl4 | 2.2130(4) |
| Zn1—Cl3 | 2.2140(4) |
| C7—N1 | 1.275(2) |
| N1—C8 | 1.4752(18) |
| C12—N2 | 1.4745(19) |
| N2—C13 | 1.276(2) |
| N2—Zn1—N1 | 92.23(5) |
| N2—Zn1—Cl4 | 115.83(4) |
| N1—Zn1—Cl4 | 103.85(4) |
| N2—Zn1—Cl3 | 101.78(4) |
| N1—Zn1—Cl3 | 118.43(4) |
| Cl4—Zn1—Cl3 | 121.378(17) |

The general molecular geometry of coordination moiety is similar to bis(iodo)-(N,N'-(2,2-dimethylpropane-1,3-diyl) bis(1-(2-chlorophenyl)methanimine))cadmium(II). However, the intermolecular interaction scheme is distinctly different in these compounds.

The Zn(II) complex contains two structurally different, weak C—H•••Cl intramolecular hydrogen bonds. See Table 3, below. In contrast, the above mentioned cadmium complex has no distinguishable intermolecular hydrogen bonds, even the weak ones. In the Zn(II) complex, the layers are extended to three-dimensional supramolecular nets via π•••π it stacking interactions (see Table 4, below).

TABLE 3

Hydrogen bond geometry of Zn(II) complex [Å, °]

| D—H•••A | d(D—H) | d(H•••A) | d(D•••A) | <(DHA) |
| --- | --- | --- | --- | --- |
| C7—H7•••Cl1 | 0.95 | 2.71 | 3.0197(16) | 99.5 |
| C13—H13•••Cl2 | 0.95 | 2.70 | 3.0180(16) | 100.6 |
| C13—H13•••Cl4$^i$ | 0.95 | 2.70 | 3.4534(15) | 136.2 |
| C16—H16•••Cl3$^{ii}$ | 0.95 | 2.64 | 3.5792(17) | 168.0 |

Symmetry transformations used to generate equivalent atoms:
$^i$x, −y + ½, z + ½;
$^{ii}$x − 1, y, z

TABLE 4

Stacking interactions in Zn(II) complex [Å, °]

| R(I)•••R(J) | Cg•••Cg | α | β | d$_p$ |
| --- | --- | --- | --- | --- |
| Cg(1)•••Cg(1)$^i$ | 4.9870(10) | 0.00(8) | 50.8 | −3.1505(6) |
| Cg(1)•••Cg(2)$^{ii}$ | 4.1933(10) | 0.00(8) | 33.6 | −3.5406(7) |
| Cg(2)•••Cg(1)$^{iii}$ | 4.1932(10) | 5.47(8) | 32.4 | 3.4931(7) |

Symmetry transformations used to generate equivalent atoms:
$^i$x, −y + ½, z + ½;
$^{ii}$x − 1, y, z.
Cg(1) and Cg(2) indicates the centroids of six-membered pyridine rings (R) containing Cl and N14 atoms respectively;
α is a dihedral angle between planes I and J;
β is an angle between Cg(I)—Cg(J) vector and normal to plane I; and
d$_p$ is a perpendicular distance of Cg(I) on ring J plane.

Example 3

The Calculated Powder Diffraction Pattern

Crystalline bis(chloro)-(N,N'-(2,2-dimethylpropane-1,3-diyl) bis(1-(2-chlorophenyl)-methanimine))-zinc(II) complex is characterized by having at least two peaks in the powder X-ray diffraction pattern (wavelength 0.154056 nm) selected from the group consisting of 8.7±0.2° 2θ, 10.7±0.2°

2θ, 14.3±0.2° 2θ, 21.2±0.2° 2θ, and 26.6±0.2° 2θ. See FIG. 5. The calculated powder diffraction pattern matches the XRD patterns for crystalline bis(chloro)-(N,N'-(2,2-dimethylpropane-1,3-diyl)bis(1-(2-chlorophenyl)methanimine))-zinc(II), which consistency demonstrates that a crystal of bis(chloro)-(N,N'-(2,2-dimethylpropane-1,3-diyl)-bis(1-(2-chlorophenyl)methanimine))-zinc(II) is isomorphous with bis(chloro)-(N,N'-(2,2-dimethylpropane-1,3-diyl)bis(1-(2-chlorophenyl)methanimine))-zinc(II) powder.

Example 4

$^1$H-NMR Spectrum Results

Figure 6:
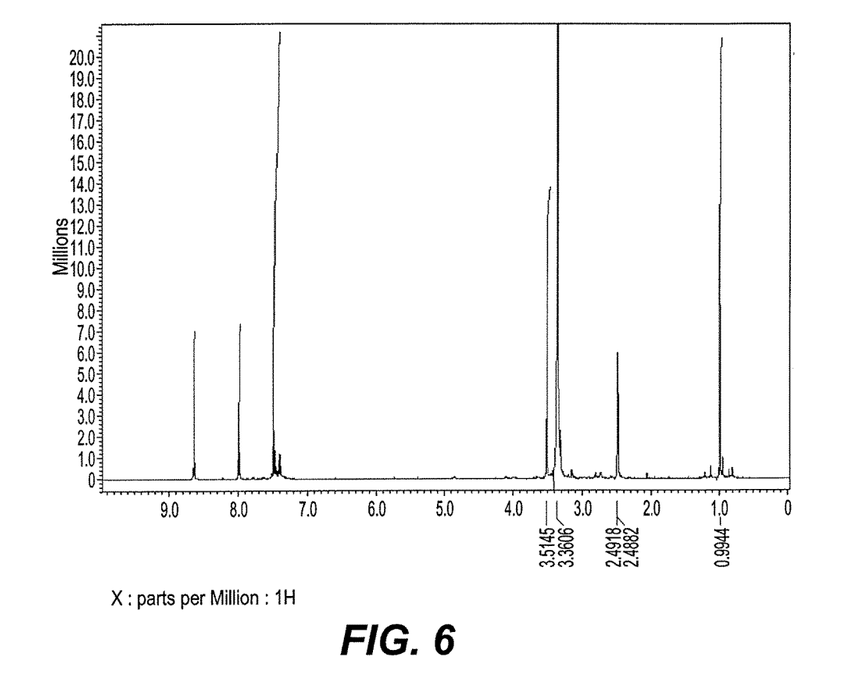
FIG. 6 is the $^1$H-NMR spectrum of anti-inflammatory zinc(II) complex in $d_6$-DMSO.

The $^1$H-NMR spectrum of the Zn(II) complex shows an azomethine proton at 8.63 ppm. The resonance signals due to —$CH_3$ and —$CH_2$ protons appear at 0.99 ppm and 3.51 ppm, respectively. The multiplet at 7.46-8.00 ppm (m, 8H, Ar—H) is attributed to the aromatic protons. See FIG. 6.

Example 5

$^{13}$C-NMR Spectrum Results

Figure 7:
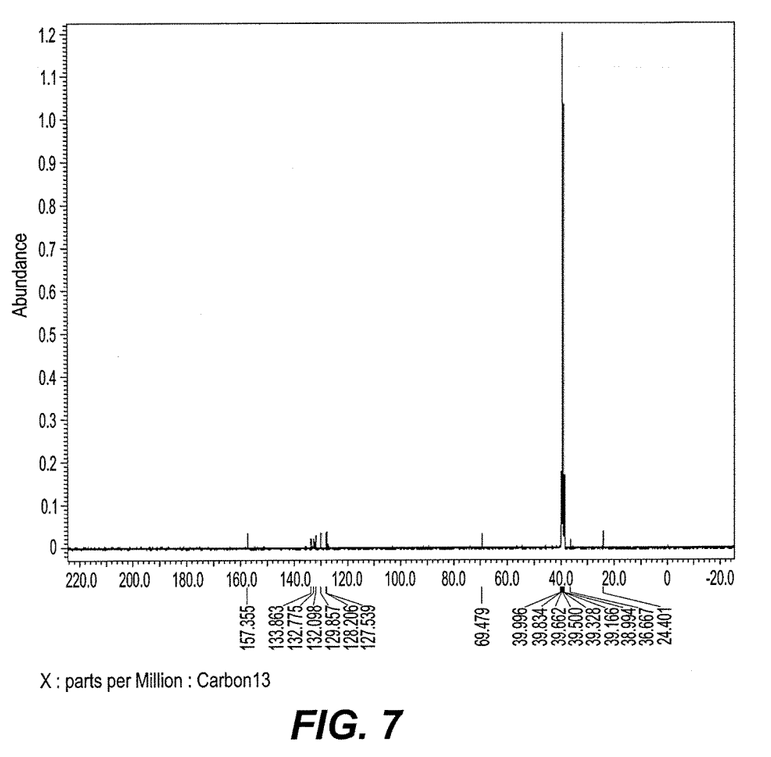
FIG. 7 is the $^{13}$C-NMR spectrum of anti-inflammatory zinc(II) complex in $d_6$-DMSO.

The $^{13}$C-NMR spectrum of the studied Zn(II) complex has the expected number of carbon signals showing azomethine (—CH═N) signal at 157.35 ppm [FIG. 7]. The carbon signals due to Ar—C—Cl and Ar—C—CH═N appear at 132.7 ppm and 133.8 ppm, respectively. The rest of the aromatic carbon signals appear at 132.0, 129.8, 128.2 and 127.5 ppm. The signal due to —$CH_2$ carbon appear at 69.4 ppm. Furthermore, the quaternary carbon appears at 36.6 ppm, whereas the —$CH_3$ carbon signal appears at 24.4 ppm. See FIG. 7.

Example 6

Crystal Structure Determination

The colourless prism crystal of the studied zinc(II) complex was sealed in a glass capillary filled with helium, and mounted on a Bruker APEXII automatic diffractometer equipped with CCD detector, for data collection. X-ray intensity data were collected with graphite monochromated $CuK_\alpha$ (λ=1.54178 □) radiation at temperature 100.0(1) K, with ω scan mode. The exposure time was 4 seconds, and reflections inside Ewald sphere were collected up to θ=72.6°. The unit cell parameters were determined from 371 strongest reflections.

Details concerning crystal data and refinement are included in Table 1. Examination of reflections on two reference frames monitored after each 20 frames measured indicated no loss of intensity during measurements. During data reduction, the Lorentz, polarization and numerical absorption corrections were applied. The structure was solved by partial structure expansion procedure.

All non-hydrogen atoms were refined anisotropically using full-matrix, least-squares technique on $F^2$. All hydrogen atoms were found from difference Fourier synthesis after four cycles of anisotropic refinement, and refined as "riding" on the adjacent atom with geometric idealisation after each cycle of refinement and individual isotropic displacement factors equal to 1.2 times the value of equivalent displacement factors of the parent non-methyl carbon atoms, and 1.5 times the value of parent methyl carbon atoms. The methyl groups were allowed to rotate about their local three-fold axes. SHELXS, SHELXL and SHELXTL crystallographic programs were used for all calculations. Atomic scattering factors were taken from the International Tables for Crystallography. Selected interatomic bond distances are listed in Table 2, and intermolecular interactions are listed in Table 3 and 4.

Example 7

Anti-Inflammatory Effects—the Testing Procedures

The crystalline zinc complex was evaluated for anti-inflammatory effects in vivo in Wistar rats, compared to the known NSAID diclofenac as a standard treatment. A graph of the comparative results is set forth in FIG. 8.

Eighteen male Wistar rats (weighing from 200-250 g) were obtained from the "Animal Care and Use Center of College of Pharmacy at King Saud University, Riyadh, Saudi Arabia". Institutional guidelines were followed for these studies. All rats were provided standard laboratory conditions of "temperature and relative humidity. The rats were kept in plastic cages and given free access to standard laboratory pellet diet and water ad libitum.

The anti-inflammatory studies were performed by the standard carrageenan-induced hind paw edema method of inducing acute swelling, known in the industry and widely reported in the literature. The rats were randomly divided into 3 groups of 6 rats. Group I rats were given carrageenan only, and served as control group. Group II and III rats were given standard diclofenac and the studied Zn(II) complex, respectively.

The standard diclofenac (4 mg/kg) and the Zn(II) complex (10 mg/kg) were administered orally half an hour before sub plantar injection of carrageenan in the right paw. Paw edema was induced by injecting 0.1 ml of a 1% w/v suspension of carrageenan in purified water. The initial and final paw volume of each rat was measured at regular interval of time (1, 2, 3, 4, 5 and 6 hours) after injection, using a digital Plethysmometer (Ugo Basile, Italy). The percent inhibition of edema produced by the diclofenac- and zinc(II) complex-treated groups was determined with respect to the control group, using the standard formula used with this type of test, as known in the industry and reported in the literature. The inhibition of inflammation was analyzed statistically by applying a student t-test, using the MS Excel 2010 spreadsheet program. A P value <0.05 was considered statistically significant.

Example 8

Anti-Inflammatory Effects—Results

The anti-inflammatory effects exhibited by diclofenac increased with time for up to about 5 hours. However, by about 5 hours after oral administration, the effects started to decrease. See FIG. 8.

Figure 8:
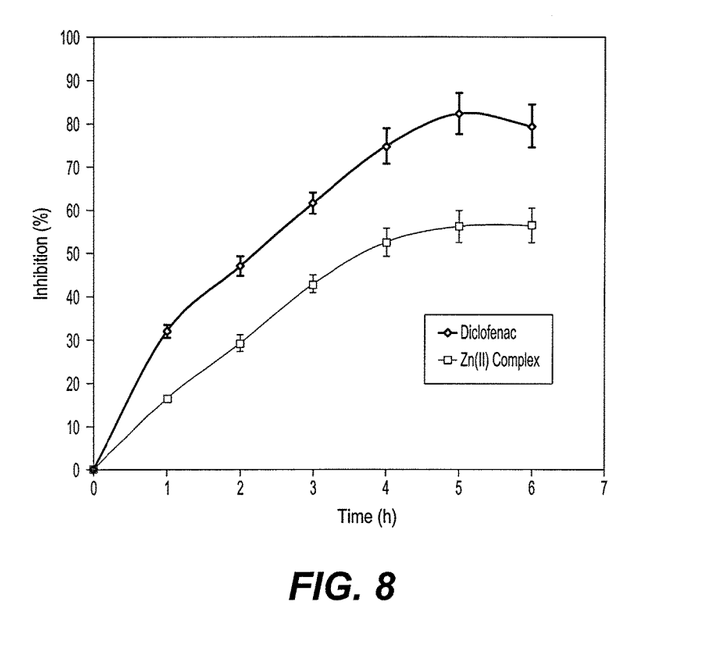
FIG. 8 is a plot of the anti-inflammatory inhibition produced by anti-inflammatory zinc(II) complex as compared to the standard, diclofenac, in Wistar rats.

The diclofenac treatment provided 82.31% inhibition of inflammation at 5 hours past oral administration. In contrast, the Zn(II) complex inhibition continued to increase for up to about 6 hour. However, after 4 hours of oral administration, the enhancement in anti-inflammatory effect was no longer statistically significant (P>0.05). The inhibition at 6 hours post oral administration was 56.39% for the Zn(II) complex.

The in vivo anti-inflammatory effects of standard diclofenac were significant in comparison with the studied Zn(II) complex at each time interval ($P<0.05$). However, the anti-inflammatory effects of the Zn(II) complex were not statistically significant in comparison with standard diclofenac ($P>0.05$).

Thus, the zinc complex presented a good degree of anti-inflammatory activity. This activity would be expected to be successful, whether treating, reducing, or preventing or reducing an increase in a patient's inflammation or the discomfort resulting from the inflammation. The anti-inflammatory effects of the studied Zn(II) complex may be due to inhibition of prostaglandins, and/or induction of proinflammatory cytokines.

It is to be understood that the anti-inflammatory zinc(II) complex is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for achieving an effect in a patient, comprising administering an effective amount of an anti-inflammatory zinc (II) complex to the patient, wherein the effect is treating inflammation or reducing swelling due to inflammation, the anti-inflammatory zinc (II) complex having the formula:

* * * * *